United States Patent
Chen et al.

(10) Patent No.: US 6,831,286 B2
(45) Date of Patent: Dec. 14, 2004

(54) METHOD FOR DETERMINING A TILT ANGLE OF AN OPTICAL PICKUP HEAD

(75) Inventors: Han-Chao Chen, Taipei (TW); Jeng-Jiun Chen, Taipei (TW); Bor-Ruey Chen, Taipei (TW)

(73) Assignee: Lite-On It Corporation, Taipei (TW)

( * ) Notice: Subject to any disclaimer, the term of this patent is extended or adjusted under 35 U.S.C. 154(b) by 0 days.

(21) Appl. No.: 10/780,920

(22) Filed: Feb. 17, 2004

(65) Prior Publication Data

US 2004/0160876 A1 Aug. 19, 2004

Related U.S. Application Data

(63) Continuation of application No. 09/938,846, filed on Aug. 24, 2001, now abandoned.
(60) Provisional application No. 60/227,714, filed on Aug. 24, 2000.

(30) Foreign Application Priority Data

Feb. 27, 2003 (TW) ........................................ 92104336 A

(51) Int. Cl.$^7$ .............................................. G01N 21/86
(52) U.S. Cl. ................. 250/559.29; 250/559.3
(58) Field of Search ......................... 250/559.29, 559.3, 250/559.37, 548, 201.5, 216; 369/53.19, 53.12

(56) References Cited

U.S. PATENT DOCUMENTS 6,282,161 B1 * 8/2001 Son et al. ................. 369/53.19

* cited by examiner

Primary Examiner—Que T. Le
(74) Attorney, Agent, or Firm—Thomas, Kayden, Horstemeyer & Risley

(57) ABSTRACT

A method for determining an emitting angle of an optical pickup head of an optical drive. A jitter inspection device comprises a jig, simulating and adjusting a tilt angle of the optical pickup head, and a jitter meter installed on the jig, inspecting jitter values at different tilt angles. A quadratic surface equation decreases the data points required for measurement to five, and enables product efficiency to raise 17%, such that the minimum jitter value and optimum tilt angle can be obtained quickly.

3 Claims, 6 Drawing Sheets

METHOD FOR DETERMINING A TILT ANGLE OF AN OPTICAL PICKUP HEAD

This is a continuation of Application Ser. No. 09/938,846, filed Aug. 24, 2001, now abandoned, which claims benefit of 60/227,714 filed Aug. 24, 2000.

BACKGROUND OF THE INVENTION

1. Field of the Invention

The present invention relates to a method for determining a tilt angle of an optical head, and in particular to a method of calculating a minimum jitter value and an optimum tilt angle of an optical pickup head.

2. Description of the Related Art

As shown in FIG. 1, the optical path of an optical pickup head $1a$ is not perpendicular to datum plane $2a$ because of component size and improper assembly, resulting in tilt angle $\theta$. In conventional methods, manufacturers perform a measuring process, in radial and tangential directions separately, gauging the relationship between jitter values and tilt angles to obtain an optimum tilt angle for the optical pickup head $1a$, in which the jitter value and its limit value are defined in CD and DVD standards. As shown in FIG. 2, the jitter value is generated by measuring the time gap between both semiperiods of data signal (T1) and clock signal (T2), calculated by Jitter=T1—T2 in accordance with the CD-ROM standard and by Jitter=(T1—T2)/T1 in accordance with the DVD standard. Another method of generating the jitter value is measurement of the pulse width (or pulse period of a Magneto-Optical Disk Drive). In addition, the jitter value and tilt angles are calculated by Jitter$(x)=a1x^2+b1x+c1$ and by Jitter$(y)=a2y^2+b2y+c2$, where x is the tilt angle in radial direction, y is the tilt angle in tangential direction, and $a1, a2, b1, b2, c1$ and $c2$ are unknown constants. The value of the tilt angle in tangential direction must be initialized to zero before the equation of Jitter(x) is obtained, and the tilt angle in radial direction is measured three times. Similarly, the value of the tilt angle in radial direction must be initialized to zero before the equation of Jitter(y) is obtained, and the tilt angle in tangential direction is measured three times.

Equations Jitter$(x)=a1x^2+b1x+c1$ and Jitter$(y)=a2y^2+b2y+c2$ are obtained by measuring three data points in one direction (radial or tangential) separately to obtain the values of $a1, a2, b1, b2, c1$ and $c2$, whereby the function "Jitter" can be completely achieved and the minimum point thereof can be determined, as shown in FIG. 3 and FIG. 4, and thereby optimum tilt angle for both directions is obtained separately. In addition, calculating of optimum tilt angle in radial or tangential direction requires measurement at least six data points, and, when the tilt angle in one direction is determined, the value of the tilt angle in another direction has to be initialized to zero.

FIG. 5 is a flowchart showing the detailed steps of conventional determination of a title angle of an optical pickup head of an optical drive, requiring much time for necessary measurement.

SUMMARY OF THE INVENTION

Accordingly, an object of the present invention is to provide a method for determining the tilt angle of an optical pickup head of an optical drive, utilizing a quadratic surface equation to measure only five data points without initializing the values of tilt angles in radial and tangential directions separately, so that a minimum jitter value and an optimum tilt angle of the optical pickup head are more easily.

According to the object described above, the present invention provides a method for determining tilt angle of the optical pickup head of an optical drive, applied in a jitter inspection device comprising a jig for simulating and adjusting a tilt angle of the optical pickup head, and a jitter meter installed on the jig for inspecting jitter values of the optical pickup head at different tilt angles, the method comprising the following steps.

The optical pickup head is measured with the jitter meter utilizing a quadratic surface equation $Z=ax^2+by^2+cx+dy+e$ using the jitter inspection device. Next, five sets of tilt angles of $(x1, y1), (x2, y2), (x3, y3), (x4, y4)$, and $(x5, y5)$, for the optical pickup head are obtained by adjusting the jig five times. A simultaneous equation is created according to the five sets of the tilt angles and their corresponding jitter values $Z1, Z2, Z3, Z4$ and $Z5$, and then, the simultaneous equation is solved to obtain the result of $a1, b1, c1, d1$ and $e1$. Next, the values of $a1, b1, c1, d1$ and $e1$ are substituted in the quadratic surface equation to create a quadratic surface equation $Z=a1x2+b1y^2+c1x+d1y+e1$. The quadratic surface equation is solved to obtain a minimum jitter value and an optimum tilt angle. Finally, a barcode is produced in accordance with the minimum jitter value as a basis for adjusting the emitting angle of the optical pickup head.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The present invention discloses a method for determining a tilt angle of an optical pickup head of an optical drive.

Figure 1:
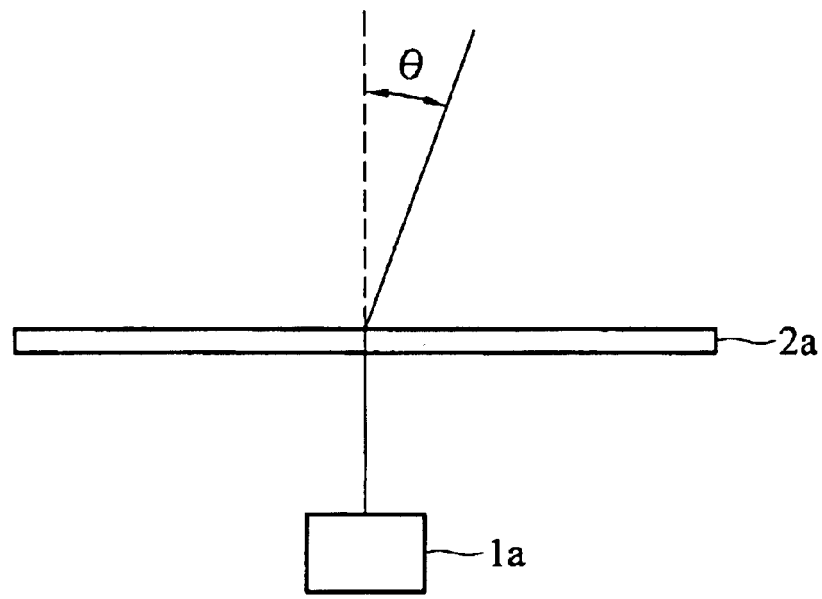
FIG. 1 is a schematic diagram showing an optical path of an optical pickup head not perpendicular to a datum plane.
Figure 2:
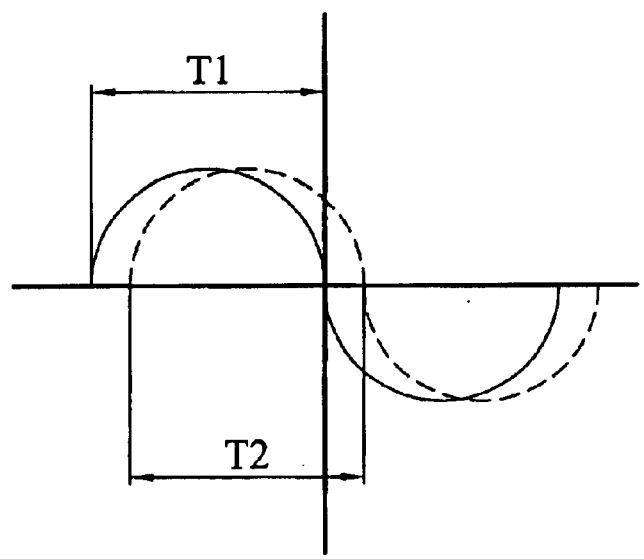
FIG. 2 is a schematic diagram defining the jitter value of an optical pickup head.
Figure 3:
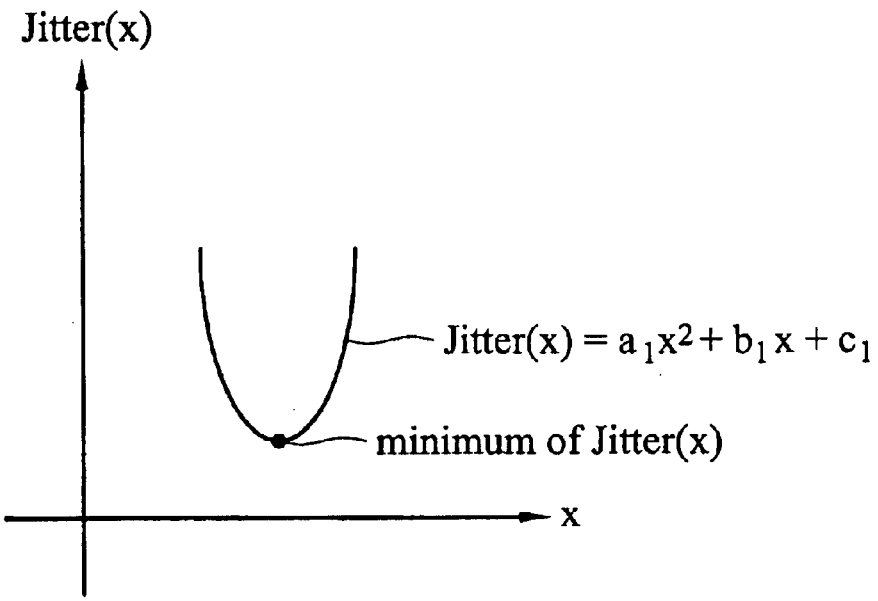
FIG. 3 is a schematic diagram showing a quadratic curve of a radial tilt angle.
Figure 4:
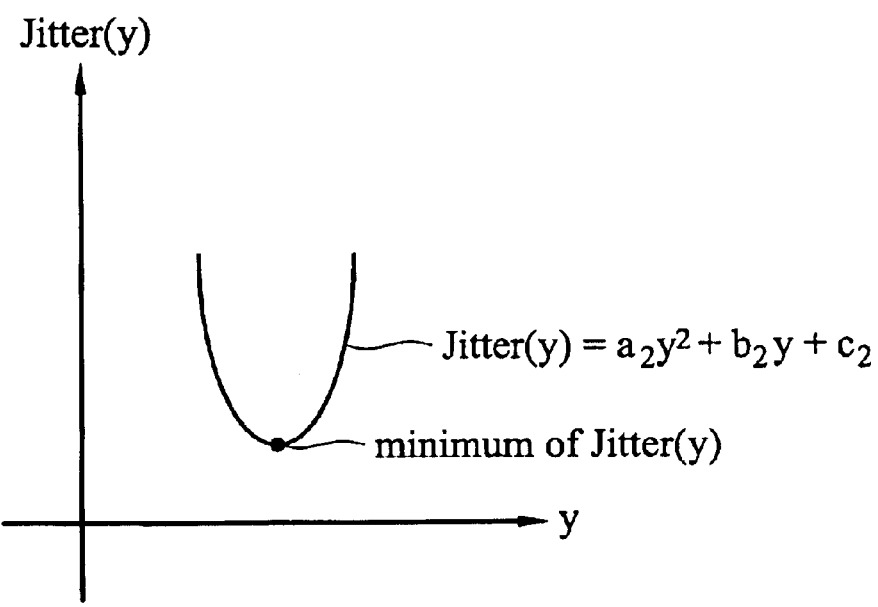
FIG. 4 is a schematic diagram showing a quadratic curve of a tangential tilt angle.
Figure 5:
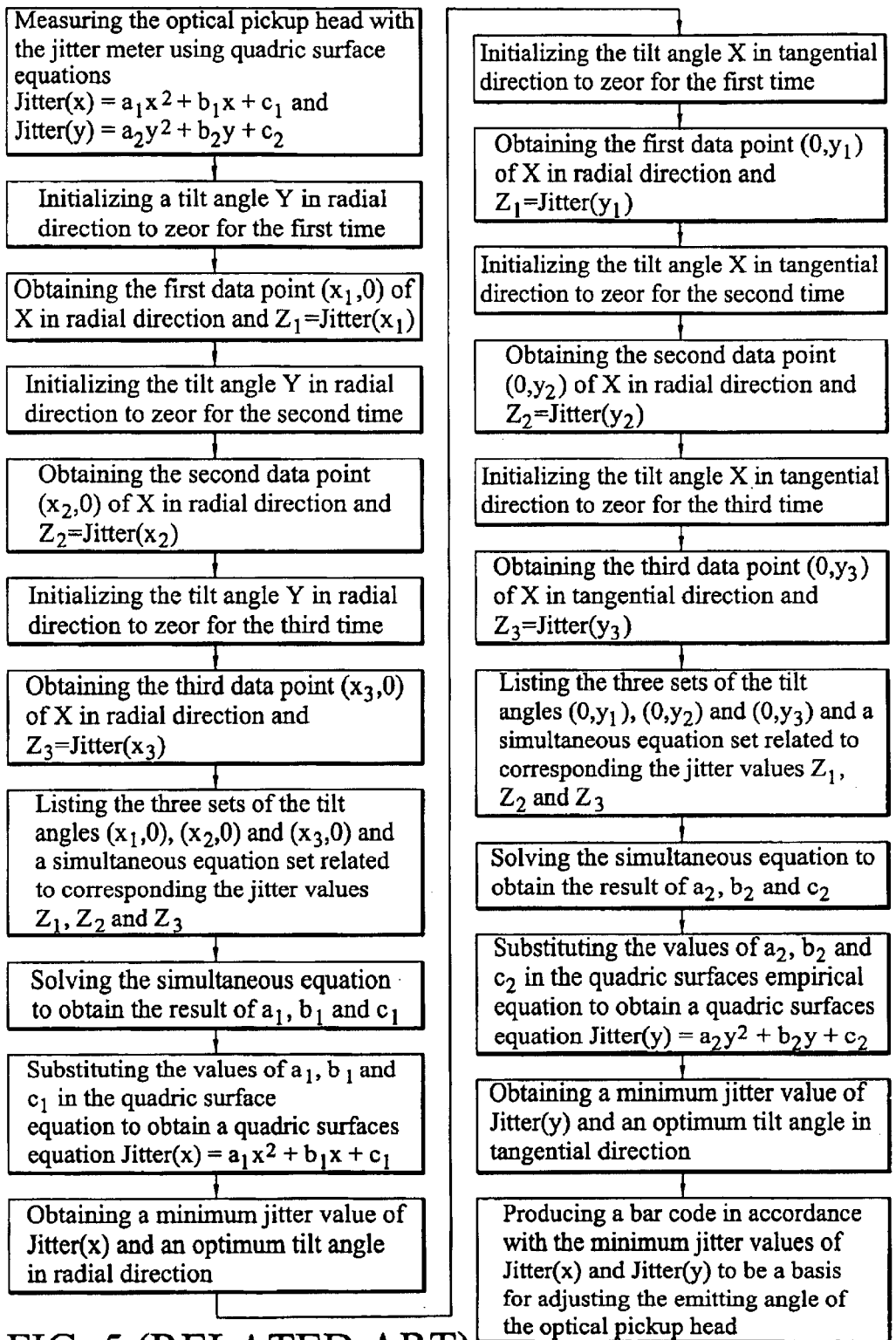
FIG. 5 is a flowchart showing the detailed steps of conventional determination of a tilt angle of an optical pickup head of an optical drive.
Figure 6:
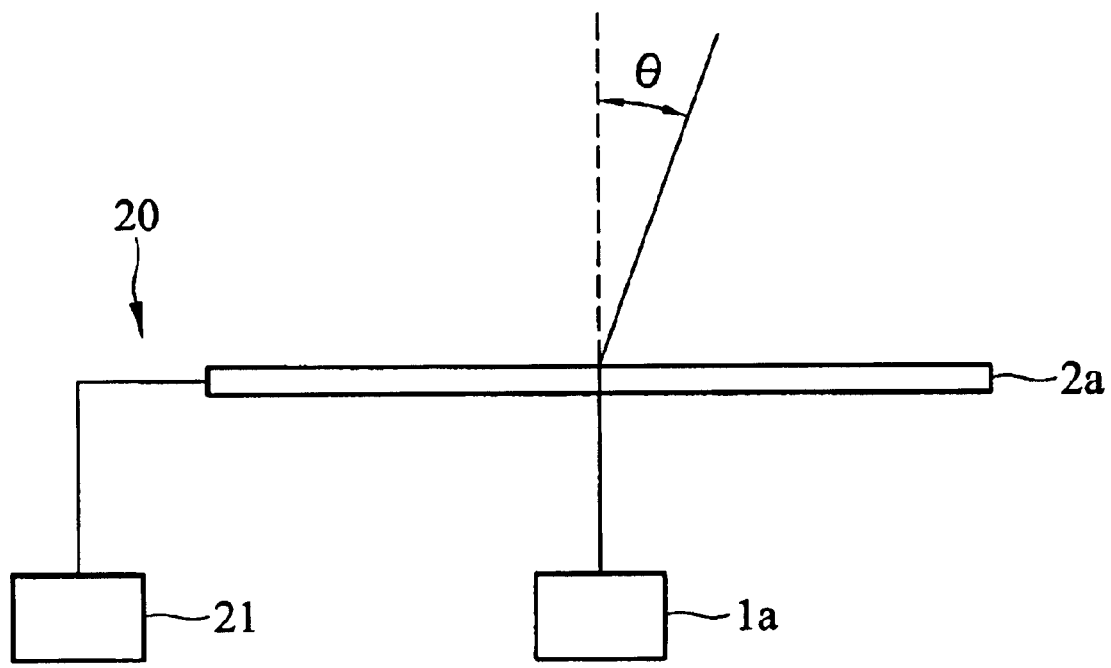
FIG. 6 is a schematic diagram showing a jitter inspection device for an optical pickup head of an optical drive according to the present invention.

FIG. 6 is a schematic diagram showing a jitter inspection device for an optical pickup head of an optical drive according to the present invention. The device comprises a jig 20, simulating and adjusting a tilt angle (e.g. $\theta$ as shown in FIG. 6) of an optical pickup head $1a$, and a jitter meter 21 installed on jig 20, inspecting jitter values with different tilt angles for optical pickup head $1a$.

Figure 7:
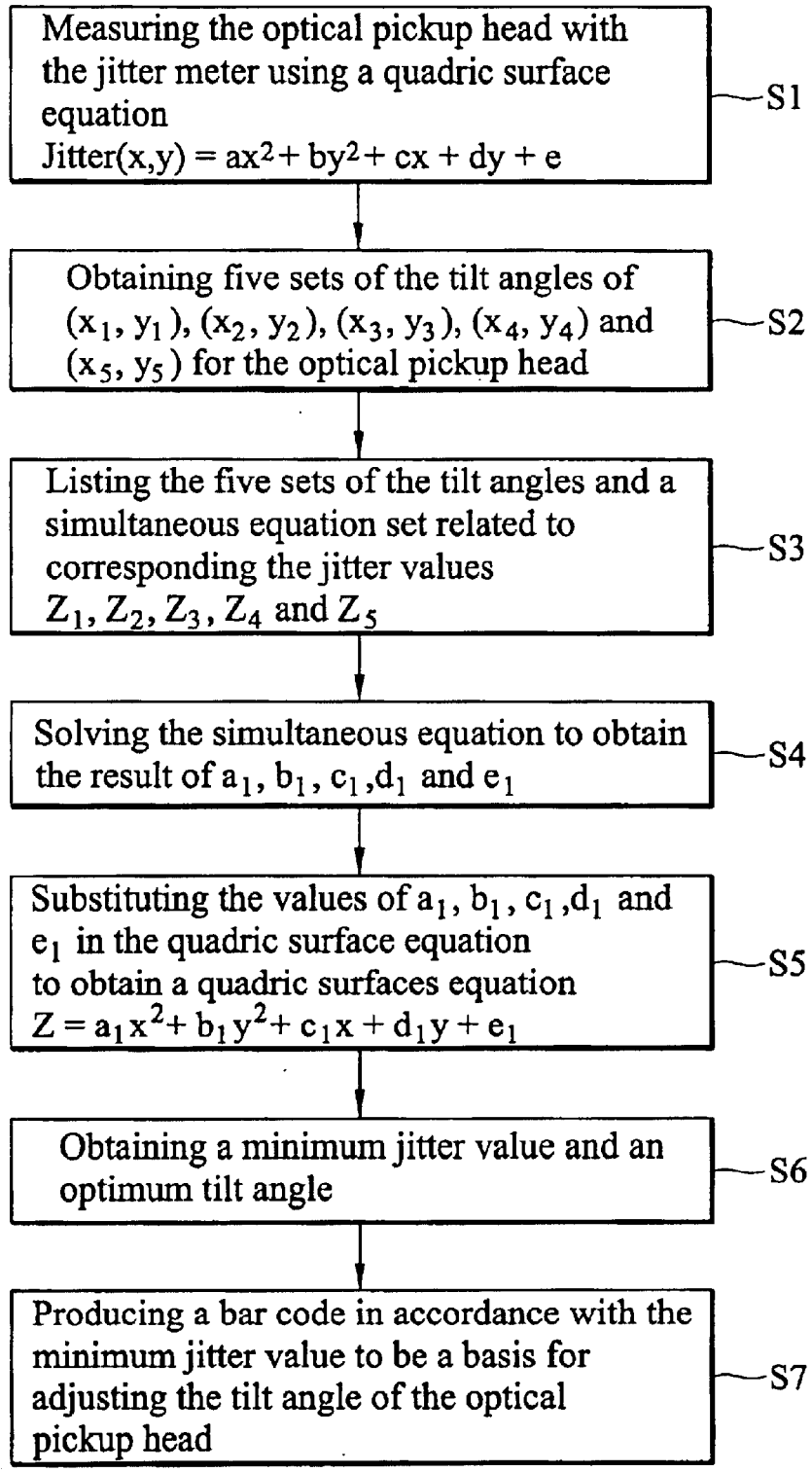
FIG. 7 is a flowchart of the method for determining a tilt angle of an optical pickup head of an optical drive according to the present invention.

FIG. 7 is a flowchart of the method for determining a tilt angle of an optical pickup head of an optical drive according to the present invention.

In step S1, a quadratic surface equation Z=Jitter(x, y) =$ax^2+by^2+cx+dy+e$ is provided, wherein x is a tilt angle in radial direction, y is a tilt angle in tangential direction, Z is the result of the function Jitter(x, y), and a, b, c, d and e are unknown constants.

In step S2, a jig is adjusted arbitrarily five times, whereby five sets of the tilt angles of (x1, y1), (x2, y2), (x3, y3), (x4, y4), and (x5, y5), for the optical pickup head are obtained, and the optical pickup head is measured simultaneously with the jitter meter to obtain the jitter values of tilt angles Z1, Z2, Z3, Z4 and Z5.

In step S3, a simultaneous equation is created according to the five sets of the tilt angles and their corresponding jitter values Z1, Z2, Z3, Z4 and Z5, creating a matrix equation, accordingly, as follows:

$$\begin{bmatrix} x_1^2 & y_1^2 & x_1 & y_1 & 1 \\ x_2^2 & y_2^2 & x_2 & y_2 & 1 \\ x_3^2 & y_3^2 & x_3 & y_3 & 1 \\ x_4^2 & y_4^2 & x_4 & y_4 & 1 \\ x_5^2 & y_5^2 & x_5 & y_5 & 1 \end{bmatrix} \begin{bmatrix} a \\ b \\ c \\ d \\ e \end{bmatrix} = \begin{bmatrix} Z_1 \\ Z_2 \\ Z_3 \\ Z_4 \\ Z_5 \end{bmatrix}$$

In step S4, the matrix equation is solved to obtain the result of a1, b1, c1, d1 and e1.

In step S5, the values of a1, b1, c1, d1 and e1, are substituted in the quadratic surface equation Z=$ax^2+by2+cx+dy+e$, in which a=a1, b=b1, c=c1, d=d1, and e=e1 to create a quadratic surface equation Z=$a1x^2+b1y^2+c1x+d1y+e1$.

Figure 8:
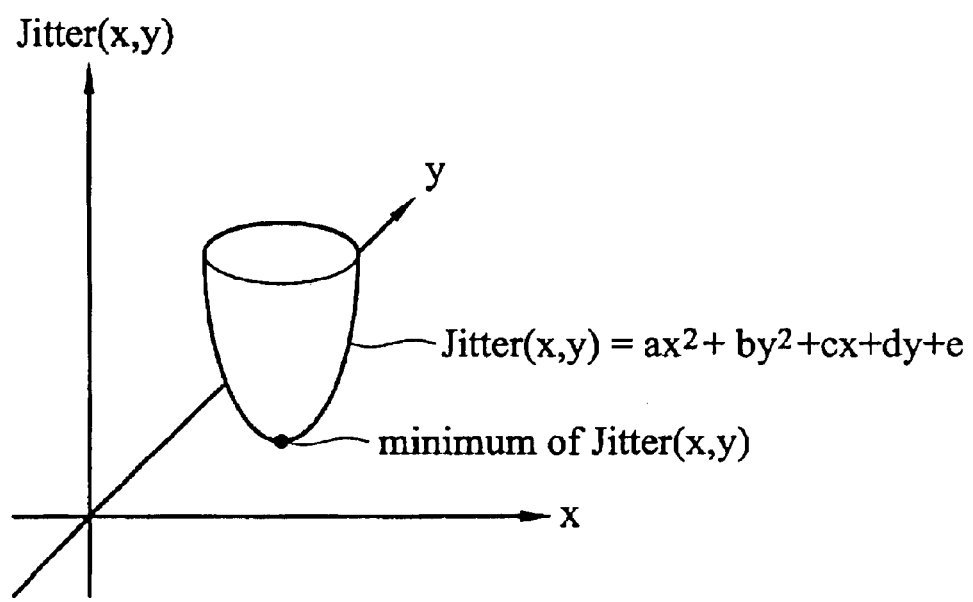
FIG. 8 is a schematic diagram showing a quadratic surface with a tilt angel in radial and tangential direction according to the present invention.

In step S6, a minimum point, the minimum jitter value, of the quadratic surface is obtained by solving the quadratic surface equation Z=$a1x^2+b1y^2+c1x+d1y+e1$, in which the minimum point is the optimum tilt angle in radial and tangential directions, as shown in FIG. 8.

In step S7, a barcode is produced in accordance with the minimum jitter value as a basis for adjusting the tilt angle of the optical pickup head.

Thus, the method of the present invention utilizes a quadratic surface equation to decrease data points required for measurement to five, raising product efficiency by 17%. In addition, by solving the simultaneous equation to enable Z1=Z2=Z3=Z4=Z5 and setting the upper limit of the jitter value, an intersection set of the optical paths for quadratic surface equations is obtained, in which the intersection set is the region to and from which optical path systems can normally write and read.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for determining a tilt angle of an optical pickup head of an optical drive, applied in a jitter inspection device comprising a jig for simulating and adjusting a tilt angle of the optical pickup head, and a jitter meter installed on the jig for inspecting jitter values of the optical pickup head at different tilt angles, comprising the steps of:

measuring the optical pickup head with the jitter meter utilizing a quadratic surface equation Z=$ax^2+by^2+cx+dy+e$ and using the jitter inspection device,
where x is the tilt angle in radial direction, y is the tilt angle in tangential direction, Z is the jitter value, and a, b, c, d, e are unknown constants;

obtaining five sets of tilt angles of (x1, y1), (x2, y2), (x3, y3), (x4, y4), and (x5, y5), for the optical pickup head by adjusting the jig five times;

creating a simultaneous equation according to the five sets of tilt angles and their corresponding jitter values Z1, Z2, Z3, Z4 and Z5;

solving the simultaneous equation to obtain the result of a1, b1, c1, d1 and e1 for unknown constants a, b, c, d, and e;

substituting the values of a1, b1, c1, d1 and e1 in the quadratic surface equation to create a quadratic surface equation Z=$a1x^2+b1y^2+c1x+d1y+e1$;

solving the quadratic surface equation to obtain a minimum jitter value and an optimum tilt angle; and producing a barcode in accordance with the minimum jitter value as a basis for adjusting the emitting angle of the optical pickup head.

2. A method for determining a tilt angle of an optical pickup head of an optical drive by measuring the optical pickup head with a jitter meter installed on a jig utilizing a quadratic surface equation Z=$ax^2+by^2+cx+dy+e$ and using the jitter inspection device, where x is the tilt in radial direction, y is the tilt in tangential direction, Z is the jitter value, and a, b, c, d, e are unknown constants, comprising the steps of:

obtaining five sets of tilt of(x1, y1), (x2, y2), (x3, y3), (x4, y4), and (x5, y5), for the optical pickup head by adjusting the jig five times;

creating a simultaneous equation according to the five sets of tilt and their corresponding jitter values Z1, Z2, Z3, Z4 and Z5;

solving the simultaneous equation to obtain the result of a1, b1, c1, d1 and e1 for unknown constants a, b, c, d, and e;

substituting the values of a1, b1, c1, d1 and e1 in the quadratic surface equation to create a quadratic surface equation Z=$a1x^2+b1y^2+c1x+d1y+e1$; and solving the quadratic surface equation to obtain a minimum jitter value and an optimum tilt angle.

3. A method according to claim 2, where in the steps further comprising:

producing a barcode in accordance with the minimum jitter value as a basis for adjusting the emitting angle of the optical pickup head.

\* \* \* \* \*